United States Patent [19]
Kruger

[11] Patent Number: 6,102,857
[45] Date of Patent: Aug. 15, 2000

[54] PHOTOACOUSTIC BREAST SCANNER

[75] Inventor: Robert A. Kruger, Indianapolis, Ind.

[73] Assignee: Optosonics, Inc., Indianapolis, Ind.

[21] Appl. No.: 09/076,968

[22] Filed: May 13, 1998

Related U.S. Application Data

[62] Division of application No. PCT/US97/17832, Oct. 1, 1997, which is a continuation of application No. 08/719,736, Oct. 4, 1996, Pat. No. 5,713,356.

[51] Int. Cl.$^7$ .................... A61B 8/00; A61B 5/00
[52] U.S. Cl. .................... 600/437; 600/459; 600/425
[58] Field of Search .................... 600/437, 425, 600/448, 459; 128/915

[56] References Cited

U.S. PATENT DOCUMENTS

| | | | |
|---|---|---|---|
| 4,059,010 | 11/1977 | Sachs | 73/596 |
| 4,222,274 | 9/1980 | Johnson | 600/448 |
| 4,233,988 | 11/1980 | Dick et al. | 128/915 X |
| 4,246,784 | 1/1981 | Bowen | 178/736 |
| 4,255,971 | 3/1981 | Rosencwaig | 73/606 |
| 4,267,736 | 5/1981 | Quate | 73/606 |
| 4,385,634 | 5/1983 | Bowen | 128/653.1 |
| 4,481,821 | 11/1984 | Chamuel | 73/617 |
| 4,484,820 | 11/1984 | Rosencwaig | 374/6 |
| 4,681,120 | 7/1987 | Kunii | 178/915 X |
| 4,874,251 | 10/1989 | Thomas et al. | 374/45 |
| 4,950,897 | 8/1990 | Mandelis et al. | 250/334 |
| 5,070,733 | 12/1991 | Nagata et al. | 73/602 |
| 5,170,666 | 12/1992 | Larsen | 73/571 |
| 5,348,002 | 9/1994 | Caro | 128/664 X |
| 5,402,786 | 4/1995 | Drummond | 128/660.01 X |
| 5,615,675 | 4/1997 | O'Donnell et al. | 128/653.1 |
| 5,657,754 | 8/1997 | Rosencwaig | 128/633 |
| 5,713,356 | 2/1998 | Kruger | 128/653.1 |

FOREIGN PATENT DOCUMENTS

| | | |
|---|---|---|
| 3925312 | 4/1990 | Germany. |
| 4446390 | 7/1996 | Germany. |
| WO97/27801 | 8/1997 | WIPO. |

OTHER PUBLICATIONS

Beard et al., Characterization of post mortem arterial tissue using time–resolved photoacoustic spectrosopy at 436, 461 and 532 nm, Phys. Med. Biol. 42 (1997) 177–198.

Shan et al., Modelling of a photoacoustic probe designed for medical applications, Ultrasonics 34 (1996) 575–577.

Ossoff et al., Computer–Assisted Surgical Techniques: A Vision for a Future of Otolaryngology—Head and Neck Surgery, Jrnl of Otolaryngology, vol. 23, No. 5 (1994) 354–359.

Chen et al., A new laser–ultrasound transducer for medical applications, Ultrasonics vol. 32, No. 4 (1994) 309–313.

Appledorn et al., Energy Depositioni Patterns in the breast at 1064 nm for Photoacoustic Ultrasound, SPIE vol. 2708 (1996) 655–664.

(List continued on next page.)

*Primary Examiner*—Francis J. Jaworski
*Attorney, Agent, or Firm*—Wood, Herron & Evans, L.L.P.

[57] ABSTRACT

Methods and apparatus for measuring and characterizing the localized electromagnetic wave absorption properties of biologic tissues (12) in vivo, using incident electromagnetic waves to produce resultant acoustic waves 26. Multiple acoustic transducers (33) are acoustically coupled to the surface of the tissue for measuring acoustic waves produced in the tissue when the tissue is exposed to a pulse of electromagnetic radiation. The multiple transducer signals are then combined to produce an image of the absorptivity of the tissue, which image may be used for medical diagnostic purposes. In specific embodiments, the transducers are moved to collect data from multiple locations, to facilitate imaging. Specific arrangements of transducers are illustrated. Also, specific mathematical reconstruction procedures are described for producing images from transducer signals.

24 Claims, 10 Drawing Sheets

OTHER PUBLICATIONS

Fang et al., Microwave Applicators for Photoacoustic Ultrasonography, SPIE vol. 2708 (1996) 645–654.

Kruger et al., Photoacoustic ultrasound (PAUS)—Reconstruction tomography., Med. Phys. 22 (10), Oct. 1995.

Liu et al., Simulation of Photoacoustic Signal Production in Human Breast Phantoms at 1064 nm, Spie vol. 2708, 1996, pp. 312–322.

Kruger, Photo–acoustic ultrasound, Med. Phys. 21(1): 127–131, 1994.

Kruger et al., Photoacoustic ultrasound: pulse production and detection of 0.5% liposyn, Med. Phys. 21(7): 1179–1184, 1994.

Kruger et al., Photoacoustic Ultrasound: Theory and Experimental Results, SPIE vol. 2134A: 114–121, 1994.

Nasoni et al., Thermoacoustic Emission by Deeply Penetrating Microwave Radiation, Proc. of IEEE Ultrasonic Symposium, 633–38, 1984.

Bowen et al., Some Experimental Results of the Thermoacoustic Imaging of Tissue Equivalent Phantom Materials, Proc. of IEEE Ultrasonic Symposium 2: 823–27, 1981.

Bowen, Radiation–Induced Thermoacoustic Soft Tissue Imaging, Proc. of IEEE Ultrasonic Symposium 2: 817–822, Jun. 1981.

Hunter et al., Acoustic signals of nonthermal origin from high energy protons in water, J. Acoust. Soc. Am. 69(9), 1557–1562, Jun. 1981.

Bowen, Acoustic Radiation Temperature of Non–Invasive Thermometry, Automedica, vol. 8, 247–267, 1987.

Hebden et al., Tomographic Imaging Using Picosecond Pulses of Light, SPIE vol. 1443, Medical Imaging V: Image Physics 294–300, 1991.

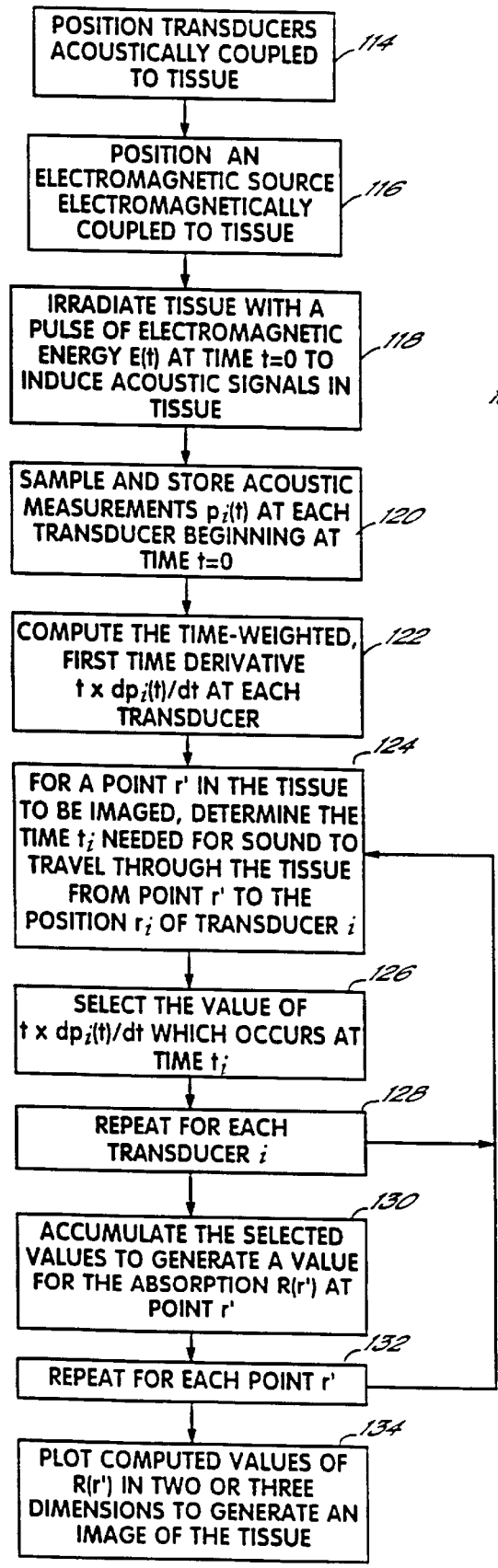
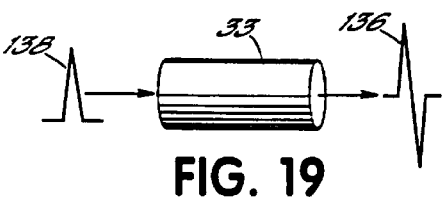
FIG. 19
FIG. 18

PHOTOACOUSTIC BREAST SCANNER

This application is a divisional of P.C.T. U.S. application Ser. No. 97/17832, filed Oct. 1, 1997 which is a continuation of U.S. Ser. No. 08/719,736 filed Oct. 4, 1996 now U.S. Pat. No. 5,713,356.

BACKGROUND OF THE INVENTION

The present invention relates to imaging properties of tissue based upon differential absorption of electromagnetic waves in differing tissue types by photo-acoustic techniques.

It is well established that different biologic tissues display significantly different interactions with electromagnetic radiation from the visible and infrared into the microwave region of the electromagnetic spectrum. While researchers have successfully quantified these interactions in vitro, they have met with only limited success when attempting to localize sites of optical interactions in vivo. Consequently, in vivo imaging of disease at these energies has not developed into a clinically significant diagnostic tool.

In the visible and near-infrared regions of the electromagnetic spectrum, ubiquitous scattering of light presents the greatest obstacle to imaging. In these regions, scattering coefficients of 10–100 $mm^{-1}$ are encountered. Consequently, useful numbers of unscattered photons do not pass through more than a few millimeters of tissue, and image reconstruction must rely on multiply-scattered photons. While efforts persist to use visible and infrared radiation for imaging through thick tissue (thicker than a few centimeters), clinically viable imaging instrumentation has not been forthcoming.

In the microwave region (100–3000 MHZ), the situation is different. Scattering is not as important, since the wavelength (in biologic tissue) at these frequencies is much greater than the "typical" dimension of tissue inhomogeneities ($\approx 1$ $\mu m$). However, the offsetting effects of diffraction and absorption have forced the use of long wavelengths, limiting the spatial resolution that can be achieved in biologic systems. At the low end of the microwave frequency range, tissue penetration is good, but the wavelengths are large. At the high end of this range, where wavelengths are shorter, tissue penetration is poor. To achieve sufficient energy transmission, microwave wavelengths of roughly 2–12 cm (in tissue) have been used. However, at such a long wavelength, the spatial resolution that can be achieved is no better than roughly ½ the microwave length, or about 1–6 cm.

In vivo imaging has also been performed using ultrasound techniques. In this technique, an acoustic rather than electromagnetic wave propagates through the tissue, reflecting from tissue boundary regions where there are changes in acoustic impedance. Typically, a piezoelectric ceramic chip is electrically pulsed, causing the chip to mechanically oscillate at a frequency of a few megahertz. The vibrating chip is placed in contact with tissue, generating a narrow beam of acoustic waves in the tissue. Reflections of this wave cause the chip to vibrate, which vibrations are converted to detectable electrical energy, which is recorded.

The duration in time between the original pulse and its reflection is roughly proportional to the distance from the piezoelectric chip to the tissue discontinuity. Furthermore, since the ultrasonic energy is emitted in a narrow beam, the recorded echoes identify features only along a narrow strip in the tissue. Thus, by varying the direction of the ultrasonic pulse propagation, multi-dimensional images can be assembled a line at a time, each line representing the variation of acoustic properties of tissue along the direction of propagation of one ultrasonic pulse.

For most diagnostic applications, ultrasonic techniques can localize tissue discontinuities to within about a millimeter. Thus, ultrasound techniques are capable of higher spatial resolution than microwave imaging.

The photoacoustic effect was first described in 1881 by Alexander Graham Bell and others, who studied the acoustic signals that were produced whenever a gas in an enclosed cell is illuminated with a periodically modulated light source. When the light source is modulated at an audio frequency, the periodic heating and cooling of the gas sample produced an acoustic signal in the audible range that could be detected with a microphone. Since that time, the photoacoustic effect has been studied extensively and used mainly for spectroscopic analysis of gases, liquid and solid samples.

It was first suggested that photoacozistics, also known as thermoacoustics, could be used to interrogate living tissue in 1981, but no subsequent imaging techniques were developed. The state of prior art of imaging of soft tissues using photoacoustic, or thermoacoustic, interactions is best summarized in Bowen U.S. Pat. No. 4,385,634. In this document, Bowen teaches that ultrasonic signals can be induced in soft tissue whenever pulsed radiation is absorbed within the tissue, and that these ultrasonic signals can be detected by a transducer placed outside the body. Bowen derives a relationship (Bowen's equation 21) between the pressure signals $p(z,t)$ induced by the photoacoustic interaction and the first time derivative of a heating functions, $S(z,t)$, that represents the local heating produced by radiation absorption. Bowen teaches that the distance between a site of radiation absorption within soft tissue is related to the time delay between the time when the radiation was absorbed and when the acoustic wave was detected.

Bowen discusses producing "images" indicating the composition of a structure, and detecting pressure signals at multiple locations, but the geometry and distribution of multiple transducers, the means for coupling these transducers to the soft tissue, and their geometrical relationship to the source of radiation, are not described. Additionally, nowhere does Bowen teach how the measured pressure signals from these multiple locations are to be processed in order to form a 2- or 3-dimensional image of the internal structures of the soft tissue. The only examples presented are 1-dimensional in nature, and merely illustrate the simple relationship between delay time and distance from transducer to absorption site.

SUMMARY OF THE INVENTION

The present invention improves upon what is disclosed by Bowen in two ways. First, the present invention uses multiple transducers to collect photoacoustic signals in parallel, and then combines these signals to form an image. This approach represents a significant advance over Bowen in that the use of multiple, parallel transducers, substantially reduces the time needed to collect sufficient information for imaging. Furthermore, while Bowen fails to suggest methodologies for creating multidimensional images, the present invention provides specific methodologies for reconstructing multidimensional images of internal tissues through the combination of multiple pressure recordings. As part of achieving these advances over Bowen, the present invention details the frequencies that might be used, the size of the multiple transducers, their geometrical relationship to one another and to the tissue, and structures for coupling sensors to the tissue.

Specifically, in one aspect, the invention provides a method of imaging tissue structures by detecting localized absorption of electromagnetic waves in the tissue. An image is formed by irradiating the tissue with a pulse of electromagnetic radiation, and detecting and storing resultant pressure waveforms arriving at the acoustic sensors. Multiple detected pressure waveforms are then combined to derive a measure of the extent to which pressure waveforms are originating at a point distant from the acoustic sensors. This step can then be repeated for multiple points to produce an image of structures in the tissue.

In a disclosed particular embodiment, the multiple pressure waveforms are combined to form an image at a point by determining a distance between the point and a pressure sensor, and then computing a value related to the time rate of change in the pressure waveform, at a time which is a time delay after the pulse of electromagnetic radiation—this time delay being equal to the time needed for sound to travel through the tissue from the point to the pressure sensor. This process, determining a distance and time delay, and then computing a value for time rate of change, is repeated for each additional pressure sensor and its pressure waveform, and the computed values are accumulated to form the measure of the pressure waveforms originating at the point. These point measurements may then be collected into a multi-dimensional image.

In one specific embodiment, the pressure sensor signal is processed by appropriate electrical circuitry so that the electrical output of the sensor is representative of the time rate of change of the pressure waveform. As a result, the value representing the time rate of change of pressure is directly available from the sensor output. To create an appropriate output, delayed versions of the output of the sensor are combined with the output of the sensor, which produces an electrical output representative of the time rate of pressure change.

In an alternative embodiment discussed below, a measure of pressure waveforms originating at a point, is generated by computing a value related to a sum of the pressure waveform detected by the acoustic transducer over the time period—where again the time period begins simultaneous with the electromagnetic irradiating pulse, and has a duration equal to the time needed for sound to travel through the tissue from the point to the pressure sensor. These steps can then be repeated for additional pressure sensors and their waveforms, and the results accumulated as discussed above to form the measure of pressure waveforms originating at the point.

In either approach, it is useful to multiply the computed time rate of change, or computed time period sum, of an acoustic transducer signal, by a factor proportional to the time delay used to produce the value. Doing so compensates for the diffulsion of acoustic energy radiated from the point as it travels through the tissue to the transducer.

In apparatus for carrying out these imaging methods, the sensors are positioned on a surface and relatively evenly spaced across the surface so as to, in combination, produce sharp multi-dimensional images through the tissue. To reduce the number of sensors required, the sensors may be moved to multiple positions while producing an image. Specifically, while the sensors are in a first position, the tissue is irradiated and the pressure waveforms from the sensors are recorded. Then the sensors are moved to a second position and the irradiation and waveform storage are repeated. In this way, each sensor can be moved to a number of positions to generate multiple waveforms. All of the stored waveforms can then be combined to generate an image of the tissue.

The sensors may be positioned on a plane and moved in a rectilinear fashion, in which case the electromagnetic irradiation source may be moved in synchrony with the sensors. Alternatively, the sensors may be positioned on a spherical surface (having a center of curvature approximately in the center of the tissue region to be imaged) which is rotated to multiple positions. In this latter case, the sensors can be advantageously positioned on the spherical surface along a spiral path, so that rotation of the sensors produces a relatively even distribution of sensor locations across the spherical surface.

To enhance acoustic coupling to the tissue, the sensors may be immersed in an acoustic coupling media, having an acoustic characteristic impedance which is substantially similar to that of the tissue to reduce reflections of acoustic waves impinging into the media from the tissue. A flexible film may be used to contain the acoustic coupling media, so that the tissue can be pressed upon the flexible film to couple acoustic waves from the tissue into the acoustic coupling media.

Similarly, the electromagnetic radiation source may be immersed in an electromagnetic coupling media having an electromagnetic characteristic impedance which is substantially similar to that of the tissue to reduce reflections of electromagnetic waves impinging into the tissue from the electromagnetic coupling media. Here again, a flexible film is used to couple electromagnetic waves from the electromagnetic coupling media into the tissue.

In one particular embodiment, both the electromagnetic radiation source and the acoustic transducers are immersed in the same coupling media, and the coupling media has a characteristic acoustic and electromagnetic impedance which is substantially similar to that of the tissue.

The electromagnetic radiation may be laser-generated radiation in the ultraviolet, visible or near-infrared band, light generated by a Xenon flash lamp, or microwave frequency radiation from a microwave antenna such as a coil. In the latter case, a microwave frequency of four hundred and thirty-three or nine hundred and fifteen MHZ may be advantageous since these frequencies are FCC approved and fall within a frequency band in which malignant and normal tissue exhibit substantially different absorptivities.

The above and other objects and advantages of the present invention shall be made apparent from the accompanying drawings and the description thereof

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 18 illustrates a second reconstruction methodology for forming a tissue image from acoustic transducer signals;

FIG. 19 illustrates the ideal impulse response of a transducer which produces an electrical output signal indicative of the first temporal derivative of an incident pressure signal;

DETAILED DESCRIPTION OF SPECIFIC EMBODIMENTS

Figure 1:
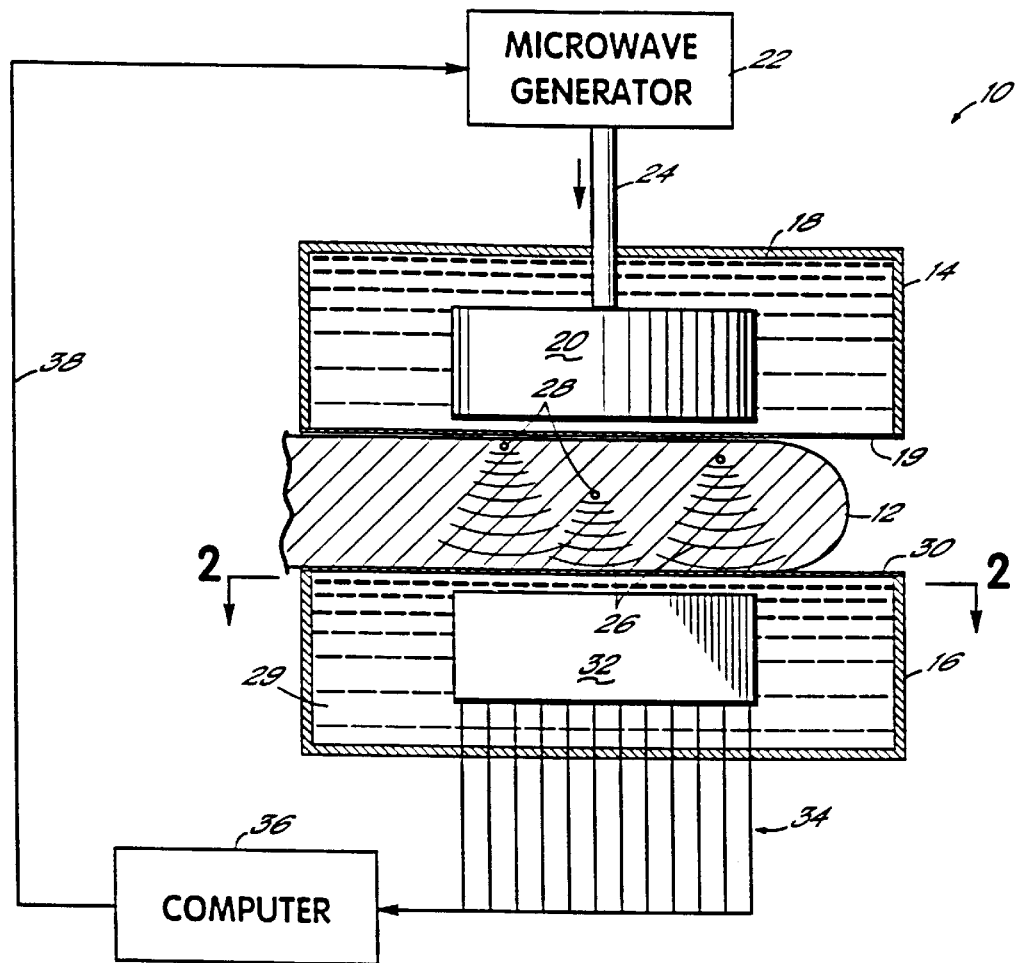
FIG. 1 is a functional block diagram of a photoacoustic scanner for scanning breast tissue in accordance with a first embodiment of the present invention.

FIG. 1 illustrates a photoacoustic breast scanner 10 in accordance with one embodiment of the present invention, which displays several key elements for successful photoacoustic scanning of the female human breast.

A human breast 12 is compressed between two coupling tanks 14, 16. Coupling tank 14 contains fluid or semi-solid media 18 having dielectric properties which are close to that of "average" breast tissue at the microwave (or radio wave) frequencies used to stimulate photoacoustic emission within the breast 12. Examples would be salinated water, alcohol or mineral oil. The media 18 is contained within tank 14 by a flexible sheet 19, for example of polyethylene, on the surface of the tank coupled to the breast 12. Sheet 19 ensures good mechanical contact between the tissue of breast 12 and the media 18 in tank 14.

Within the top coupling tank is a microwave antenna 20. A microwave generator 22, i.e., a source of pulse microwave or radio wave energy, is coupled to antenna 20 through a transmission line 24. (One suitable microwave generator is a Hewlett-Packard model 8657B tunable generator, coupled to a 200 Watt RF amplifier available from AMP Research.) Antenna 20 is large enough to irradiate all or a large fraction of the breast volume to be imaged. A cylindrically-shaped coil antenna, three to nine inches in diameter would be suitable. Further details on waveguides which can be used as microwave radiators can be found in Fang et al., "Microwave Applicators for Photoacoustic Ultrasonography", Proc. SPIE 2708: 645–654, 1996, which is incorporated by reference herein in its entirety.

The purpose of dielectric coupling media 18 and sheet 19 is to improve the penetration of the microwave energy into the breast tissue. Because breast 12 is compressed against the surface of tank 14, there is a continuous interface between coupling media 18 and the tissue of breast 12, uninterrupted by air gaps. An air gap, or any other physical discontinuity having a corresponding discontinuity in dielectric properties, will cause a large fraction of the microwave energy to reflect away from the interface (and thus away from the surface of the breast), rather than penetrate into the breast. By matching the dielectric properties of the breast and media 18, and eliminating air gaps, such discontinuities are reduced, improving microwave penetration into breast 12.

As noted above, microwave generator 22 delivers short-duration pulses of radiation to breast 12. These bursts should last anywhere from 10 nanoseconds to one microsecond, e.g., 0.5 microseconds. Each radiation burst causes localized heating and expansion of the breast tissue exposed to the microwave energy. Tissue heating and expansion will be greatest in those regions of the breast tissue which are most absorptive of the microwave energy. If a region of tissue within breast 12 (e.g., a tumor) is particularly more absorptive than the surrounding tissue, the region will expand relatively more rapidly and extensively than the surrounding tissue, creating an acoustic wave which will propagate through the tissue. These acoustic waves are manifested as longitudinal pressure waves, containing acoustic frequencies ranging from very low frequencies to approximately the reciprocal of the electromagnetic pulse length. For a one-half microsecond irradiation pulse, this maximum acoustic frequency would be 2 million cycles per second, or two megaHertz (MHZ).

Any of several different microwave frequencies may be used, but frequencies in the range of 100–1000 MHZ are likely to be particularly effective. At these frequencies, energy penetration is good, absorption is adequate, and differential absorption between different types of tissue, e.g. fat and muscle, is high. It has also been reported that the ratio of absorbed energy in cancerous relative to normal breast tissue is enhanced in this frequency range, peaking at 2–3 between about 300–500 MHZ. (See, e.g., Joines, W. T. et al, "The measured electrical properties of normal and malignant human tissues from 50–900 MHZ", Medical Physics, 21(4) :547–550, 1994.) The frequency of 433 MHZ, specifically, has been approved by the FCC for use in hyperthermia treatments, and accordingly is available and may be used in photoacoustic imaging in accordance with the present invention. Imaging might also be performed at the FCC approved frequency of 915 MHZ. Furthermore, it has been reported that the electrical conductivity of malignant tissue and normal tissue may vary by a factor of fifty. Accordingly, low frequency electromagnetic radiation could also be used to stimulate varied energy absorption and acoustic responses in tissue.

FIG. 1 illustrates the acoustic wavefronts 26 produced by electromagnetic irradiation of three absorptive regions 28 within the breast 12. It will be understood that the acoustic waves produced by regions 28 are omnidirectional; however, for clarity only those wavefronts directed toward coupling tank 16 have been illustrated. These acoustic waves travel through the tissue at a velocity of sound propagation $v_s$ which is approximately 1.5 mm/µs.

Coupling tank 16 is filled with media 29 having an acoustic impedance and velocity of sound propagation which are close to that of a "typical" human breast. Distilled and deionized water is an effective media for this purpose. Media 29 is retained within tank 16 by a thin sheet 30, such as polyethylene. Breast 12 is compressed against sheet 30, thus ensuring good mechanical coupling from breast 12 to media 29 within tank 16, and allowing acoustic energy to freely pass from breast 12 into tank 16. As with sheet 19 for tank 14, good mechanical coupling through sheet 30 and the similar acoustic characteristics of breast 12 and media 29 enhances transmission of acoustic signals out of breast 12 and into media 29 and reduces acoustic wave reflections at the surface of breast 12.

Figure 2:
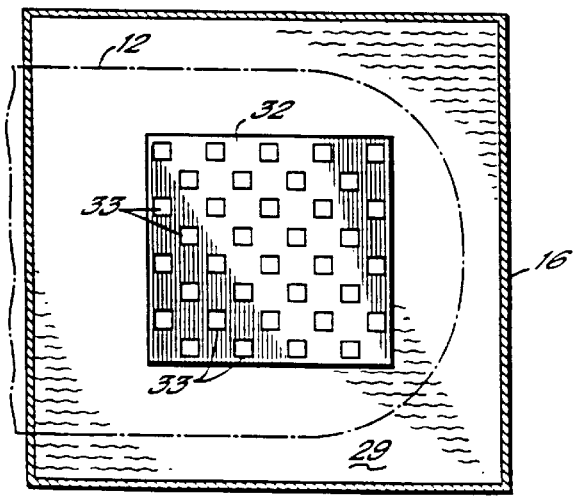
FIG. 2 is a top view of one embodiment of a transducer array for the scanner of FIG. 1.

An array 32 of N acoustic transducers is located in tank 16. Several useful array geometries are discussed herein and can be used successfully in the embodiment of d be at least about two inches across, and might for some applications be as large as twelve inches across. The transducers should be evenly spaced across the array. FIG. 2, for example, is a view illustrating an essentially planar array 32, approximately three inches square, bearing forty-one individual transducers 33 which can be used as the transducer array 32 in tank 16 of FIG. 1. Other arrangements of transducers will be discussed below.

Transducers in array 32 detect acoustic pressure waves that are induced within the breast by the short irradiation pulse, and travel from emission sites (e.g., regions 28) at the velocity of sound in tissue. The transducers are fabricated so as to be most sensitive to sonic frequencies just below the maximum frequency stimulated by the irradiation pulse noted above.

The N transducers in array 32 are coupled through N electronic signal lines 34 to a computer circuit 36. Computer 36 is further connected through a control line 38 to activate microwave generator 22 to produce a pulse of microwave energy. Following each pulse of radiation, the time-dependent, acoustic pressure signals recorded by each of the N transducer elements are electronically amplified, digitized and stored within computer 36. The recorded pressure signal from transducer i will be referenced hereafter $p_i(t)$.

For sufficient resolution, the pressure signals should be digitized to a resolution of 8–12 bits at a sampling rate of at least 5–20 MHZ, but higher resolutions and sampling rates could be used. The amplifier should have sufficient gain so that the analog thermal noise from the transducer is greater than ½ LSB of the span of the analog-to-digital converter, or greater. Assuming the amplifier/transducer circuit has an equivalent resistance of 50 Ohms, and the amplifier has a bandwidth of approximately 4 MHZ, thermal noise will produce a signal magnitude of approximately 2µ volts. Suitable resolution can be achieved by amplifying transducer signals with a 5 MHZ, 54 dB preamplifier available from Panametrics, and digitizing the amplified signals with an 8-bit, 20 MHZ sampling rate analog-to-digital converter with a ±0.2 volt input span, manufactured by Gage Electronics. Additionally, adjustable high pass filtering at 0.03, 0.1 and 0.3 can be added as needed to achieve desired signal to noise performance.

Figure 3:
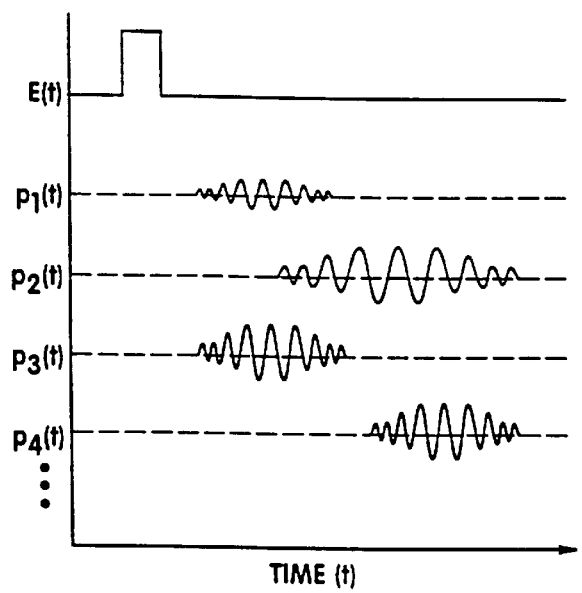
FIG. 3 illustrates the waveforms produced in the scanner of FIG. 1.

As an example, FIG. 3 illustrates the pressure signals $p_i(t)$ that might be produced by four hypothetical transducers in response to pressure waves produced by a short duration of electromagnetic irradiation of tissue. FIG. 3 shows the signal E(t) produced by computer circuit 36 (FIG. 1) on control line 38, which has a brief pulse, which causes microwave generator 22 to produce a corresponding pulse of microwave energy. The resulting acoustic signals produced within breast 12 are subsequently received by each of the transducers, producing signals $p_i(t)$ having differing relative magnitudes and timing, as illustrated.

Figure 4:
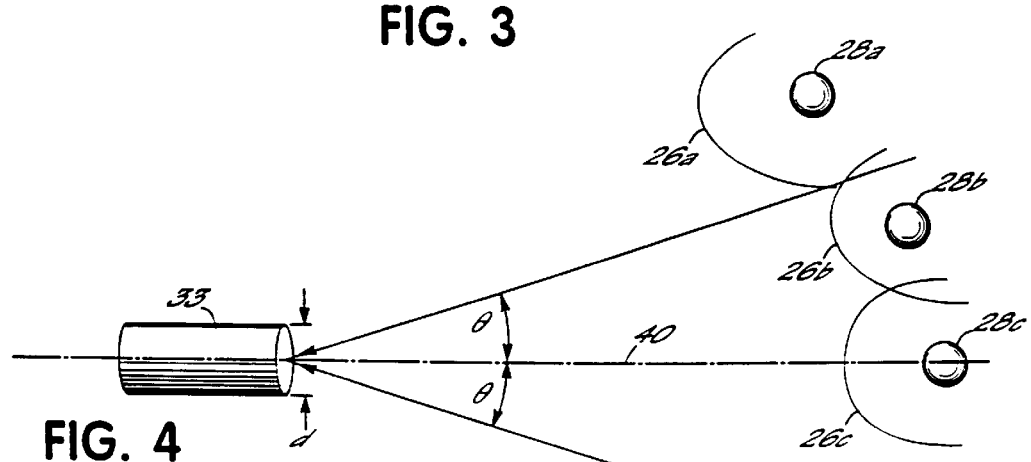
FIG. 4 illustrates the spatial response of pressure transducers used in a photoacoustic scanner such as that of FIG. 1.

It is important that the transducers be small enough so that they are sensitive to sonic waves that impinge upon the transducers from a wide angle. Referring to FIG. 4, three hypothetical absorbing regions 28a, 28b and 28c are shown in greater detail, along with the respectively corresponding wavefronts 26a, 26b and 26c emitted by these regions, toward a transducer 33. Upon irradiation, each region 28 is the origin of an acoustic pressure wave that travels in all directions. Part of each wave reaches transducer 33 after a delay time.

Transducer 33 is a piezoelectric ceramic chip (or a suitable alternative) having a cross-sectional diameter d exposed to regions 28a, 28b and 28c. Electrical contacts (not shown) attached to the exterior of transducer 33 detect an electrical waveform produced by the chip in response to mechanical vibration, as a result of the piezoelectric property of the ceramic chip.

Because the acoustic energy is transmitted in a wave, transducer 33 is not equally sensitive to the pressure waves from the three absorptive regions. The transducer is most sensitive to acoustic waves from region 28c, which lies on axis 40 of transducer 33 (axis 40 being defined by the direction that lies at a 90° angle to the front surface of transducer 33). Transducer 33 is less sensitive to acoustic waves from region 28b because this region is off of axis 40. Past a certain maximum angle, θ, away from axis 40, transducer 33 is substantially insensitive to pressure waves such as those from region 28a.

Maximum angle θ is given approximately by the relationship $\sin(\theta) \approx v_s\tau/d$, where $v_s$ is the velocity of sound in the relevant medium (here, tissue), τ is the irradiation pulse length and d is the diameter of the transducer. If a relatively large volume is to be imaged, then θ should be as large as possible (small d), but if d is too small, the transducer will produce a signal too weak to be electrically detectable without excessive noise. In general, the transducer diameter should be in the range of $v_s\tau < d < 4v_s\tau$. The velocity of sound in tissue is approximately 1.5 mm/µs. Thus, for a nominal pulse width, τ, of 1 µs, d should be in the range of approximately 1.5 to 6.0 millimeters.

Figure 5:
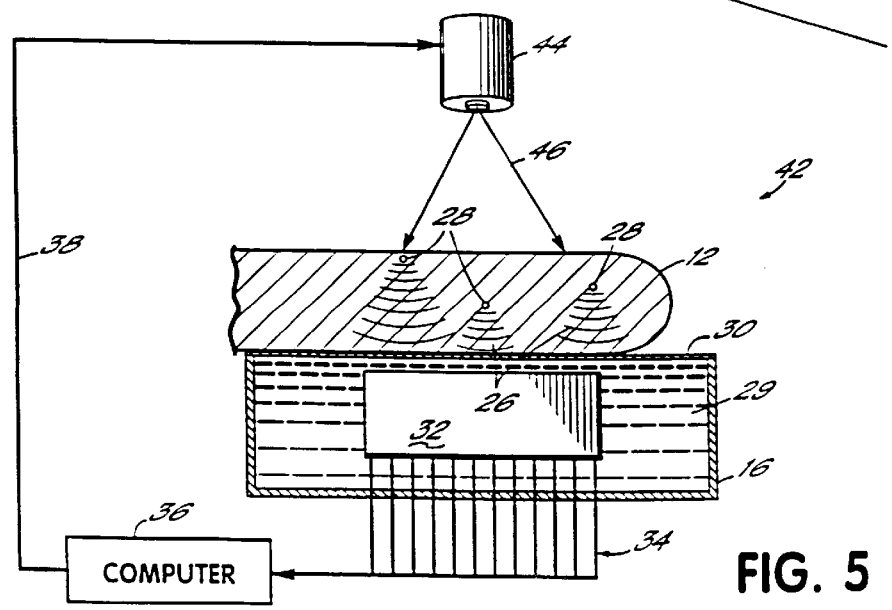
FIG. 5 is a second embodiment of a photoacoustic breast scanner in accordance with the present invention, using a laser or flash tube source of electromagnetic energy.

FIG. 5 illustrates a second embodiment of the invention identical in structure to FIG. 1 with the exception that a pulsed source 44 of visible or infrared radiation 46 is used to irradiate the breast 12 instead of a microwave antenna. Also, a coupling media may not be needed due to the close m1.064 µm, pulse width<10 nsec, 250 mJ/pulse), positioned approximately 50 mm from the regions in the tissue to be imaged and collimated to a 25–100 mm diameter beam.

Alternatively, radiation source 44 may be a flashtube energized by a pulsing power supply, such as a xenon flashtube and power supply from Xenon Corp., Woburn, Mass., which can produce a radiation pulse with a 1 $\mu$sec rise time, followed by a decaying tail with a 4 $\mu$sec time constant. A cylindrically curved, reflective surface (e.g., from Aluminum foil) may be used with the flash tube to direct radiation from the flash tube into the breast 12.

Figure 6:
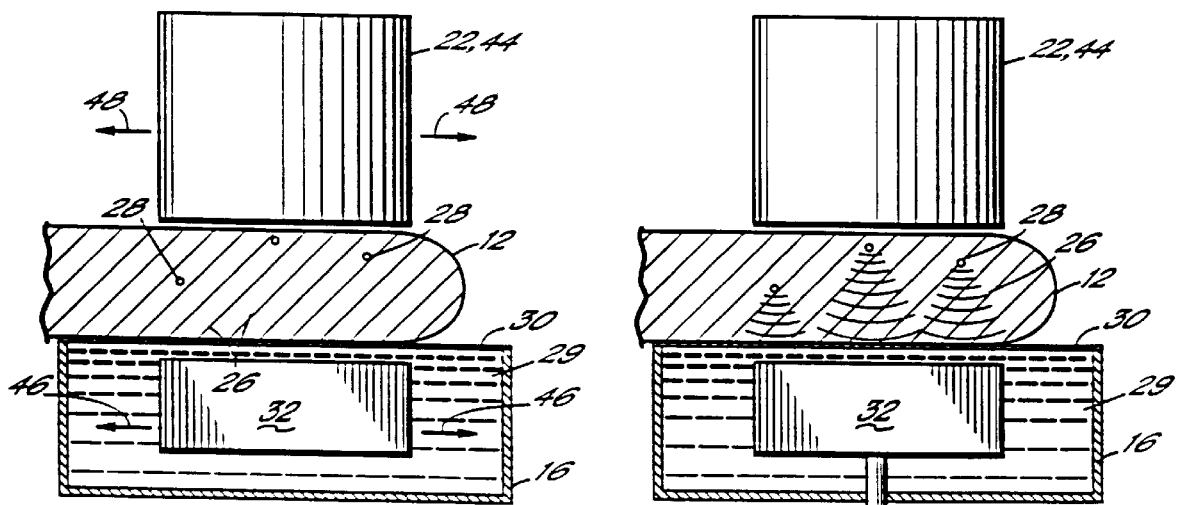
FIG. 6 is an embodiment of a transducer array and electromagnetic source for a scanner such as that of FIG. 1, configured for rectilinear scanning motion.

As noted above, array 32 is preferably of a sufficient size to image a substantial area of tissue. In some applications, however, the tissue to be imaged may be larger than array 32. Referring to FIG. 6, in such situations, array 32 and the radiation source (antenna 22 or laser or flashlamp 44) may be synchronously scanned in a rectilinear fashion as indicated by arrows 46 and 48. At each respective position of the radiation source and array 32, photoacoustic data is collected and used to develop a corresponding image. The images may then be combined or superimposed to produce a complete image of the breast 12. In this embodiment, scanning the transducer array produces the effect of increasing the transducer array size, and increases the angular sampling of the breast by the transducer array.

Figure 7:
FIG. 7 is an embodiment of a transducer array and electromagnetic source for a scanner such as that of FIG. 1, configured for rotational scanning motion.

Referring to FIG. 7, in another alternative embodiment of the present invention, the transducer array 32 is rotated during the data acquisition, as indicated by arrow 50. Here again, the breast 12 is irradiated by microwave, visible or infrared radiation from an antenna 22, or laser or flash tube 44. At each angular position of the transducer array, photoacoustic data is collected by the transducers and used to develop a corresponding image. The images may then be combined or superimposed to produce a complete image of the breast 12. In this embodiment, rotating the array 32 has the effect of increasing the effective number of transducer elements.

Figure 8:
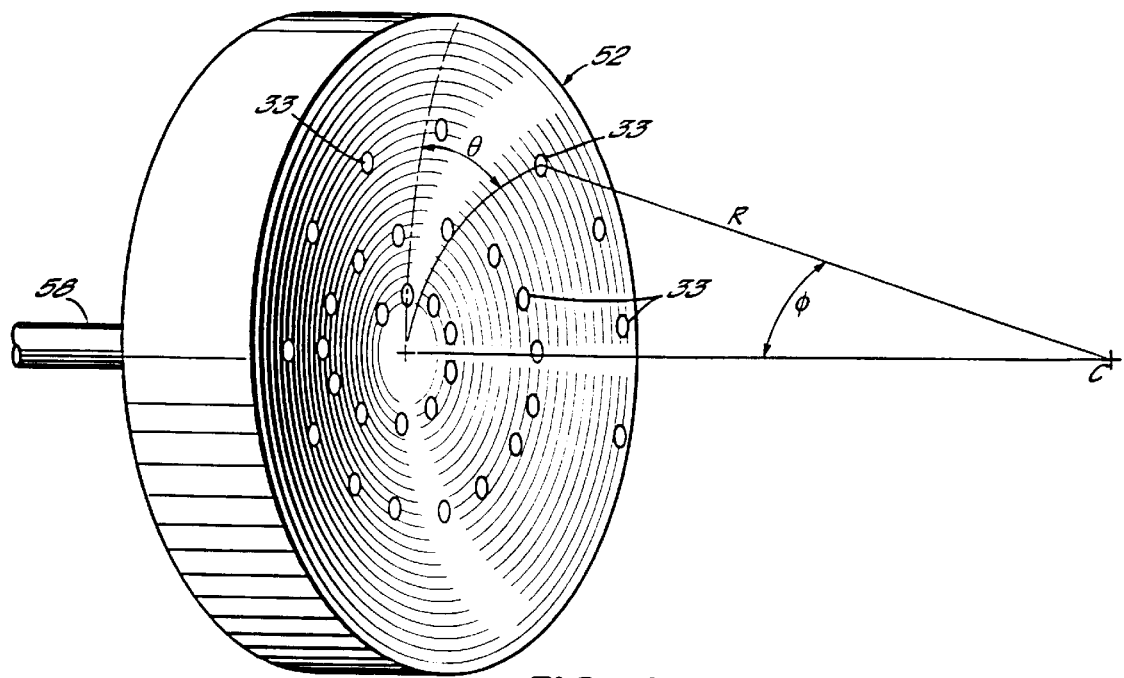
FIG. 8 is a particular embodiment of a rotationally scanning transducer array, formed on a spherical surface, illustrating the positioning of the transducers on the spherical surface of the array.

FIG. 8 illustrates a specific embodiment of a rotating transducer array wherein the transducers are arranged in a spiral pattern on a spherically curved surface 52. The radius of curvature of the surface 52 is R and the diameter of the array is D.

The position of each of the transducers in the spiral array, relative to the center C of curvature of surface 52, can be detailed with reference to FIG. 8. The position of each transducer 33 is given by three spherical coordinates $(r,\theta,\phi)$ as is illustrated in FIG. 8. Each of the N transducers 33 is on the spherical surface (at a radius R), located at a unique $(\theta,\phi)$, and is oriented on the surface with its axis 40 (see FIG. 4) passing through the center C of the radius of curvature of the spherically curved surface 52. The $\phi$ positions of the transducers 33 range from a minimum angle of $\phi_{min}$ to a maximum angle of $\phi_{max}$. It is desirable to maximize this range of angles, i.e., so that $\phi_{max}-\phi_{min}$ is as large as possible, since doing so will enhance the extent to which features in the imaged tissue can be reconstructed in multiple dimensions. (In some embodiments, $\phi_{max}-\phi_{min}$ typically must be less than 45°; however, in the embodiment of FIG. 13, $\phi_{max}-\phi_{min}$ approaches 90°.)

The spiral array will be rotationally stepped to each of M positions during data acquisition, uniformly spanning 0<$\theta$<360°. The $(\theta,\phi)$ positions of each of the N transducers are chosen so that after scanning, the locus of N×M transducer locations produced by the M rotational steps are distributed approximately uniformly over the spherical surface.

To accomplish uniform distribution of transducer locations over the spherical surface of the array, the $\theta$-positions of the transducers are given as $\theta_i=i\cdot(360/N)\cdot(k+(\sin\theta_{min}/\sin\theta_{max}))$, where $\theta_i$ is the $\theta$-position of the i-th transducer ($1 \leq i \leq N$), and k is an arbitrary integer. The $\phi$-positions of the transducers are given recursively as $\phi_{i+1}=\phi_i+(\alpha/\sin(\phi_i))$, where $\alpha$ is a constant that depends on the radius of curvature of the spherical array and the diameter of the transducer, and $\phi_1=\phi_{min}$.

Figure 9:
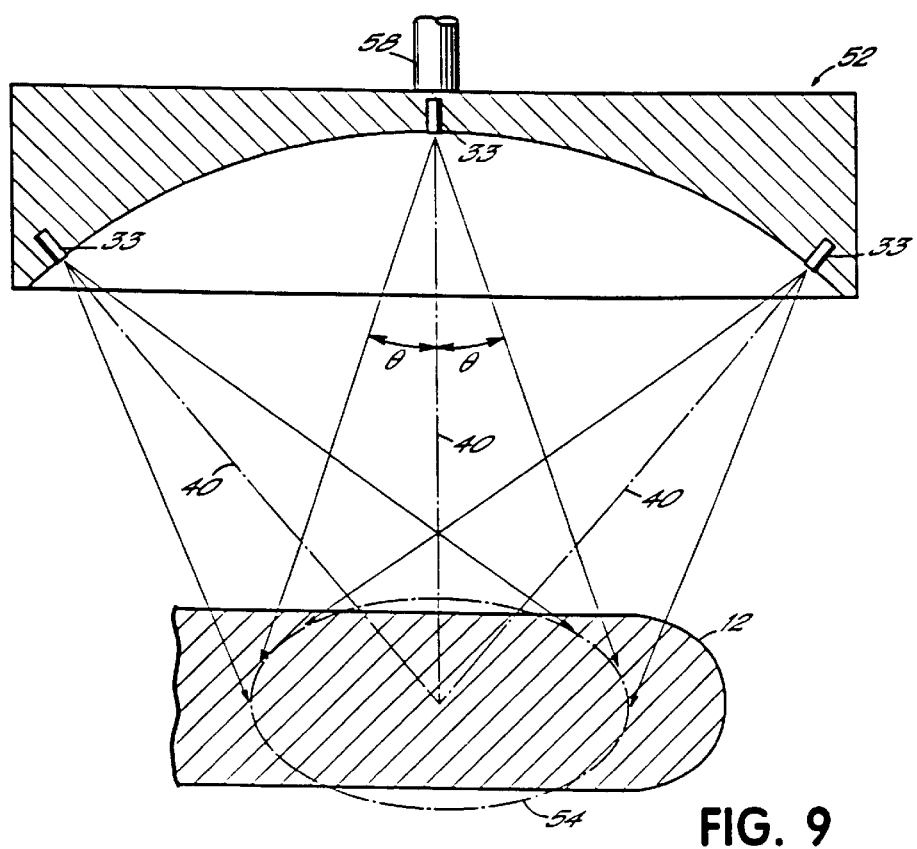
FIG. 9 illustrates the axial alignment of the transducers on the spherical surface of the array of FIG. 8.
Figure 10:
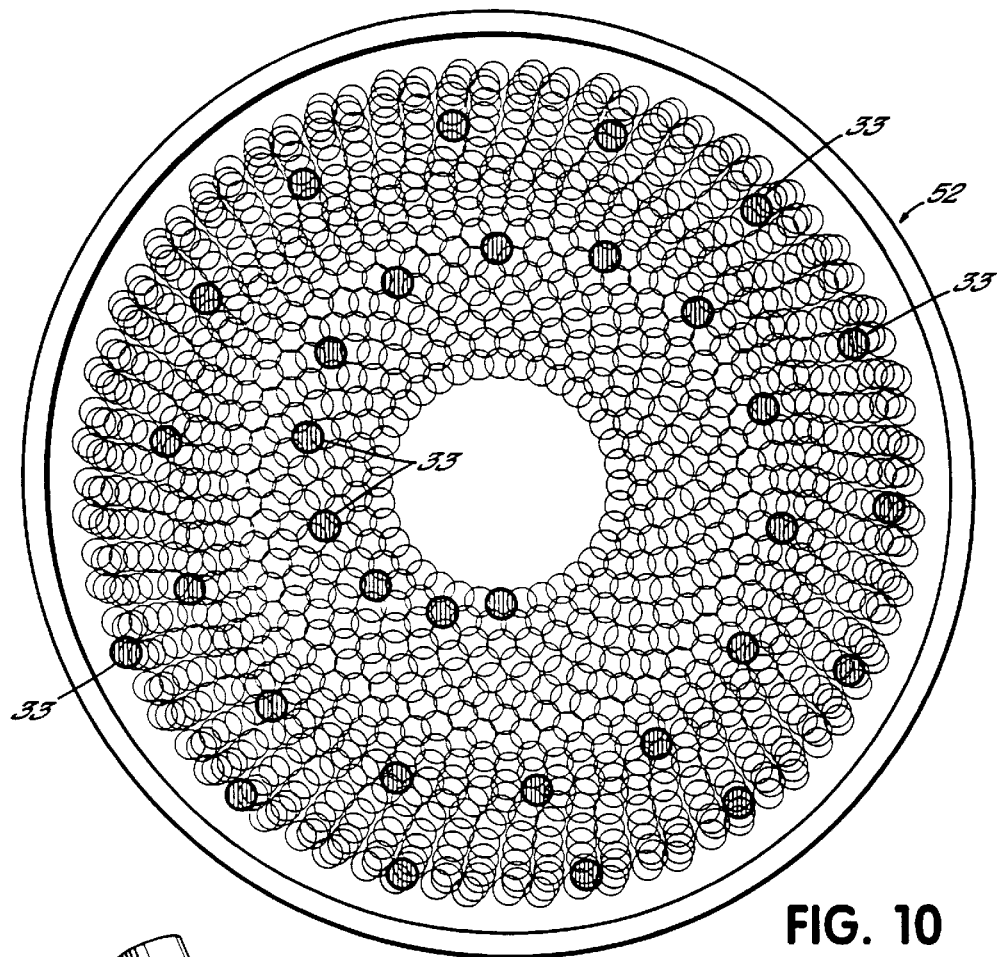
FIG. 10 illustrates the locus of transducer positions brought about through rotational scanning of the array of FIG. 8.

Two features of the rotationally scanned, spherical-spiral array are illustrated in FIGS. 9 and 10. FIG. 9 illustrates the convergence of the axes 40 of the N transducers 33 to a single point within the breast. The convergence insures that the regions to which each of the N transducers is most sensitive (see FIG. 4) will have a high degree of overlap, in an area 54 centered within the tissue under study. Also evident is the wide range of angles $\phi$ spanned by the transducer array.

FIG. 10 illustrates the nearly uniform distribution of the locus of transducer locations produced by rotation of a spherically curved surface 52 containing an array of N=32 transducers arranged in a spiral, when stepped to 32 evenly spaced angles of rotation $\theta$ in accordance with the foregoing. Referring to FIG. 10, one position of the 32 transducer elements is shown in cross-hatching. The remaining 31 positions of the transducers arrived at by $\theta$ rotation of surface 52, are illustrated in outline. As is apparent from FIG. 10, a nearly uniform distribution of the transducer locations across the spherical surface is achieved.

Figure 11B:
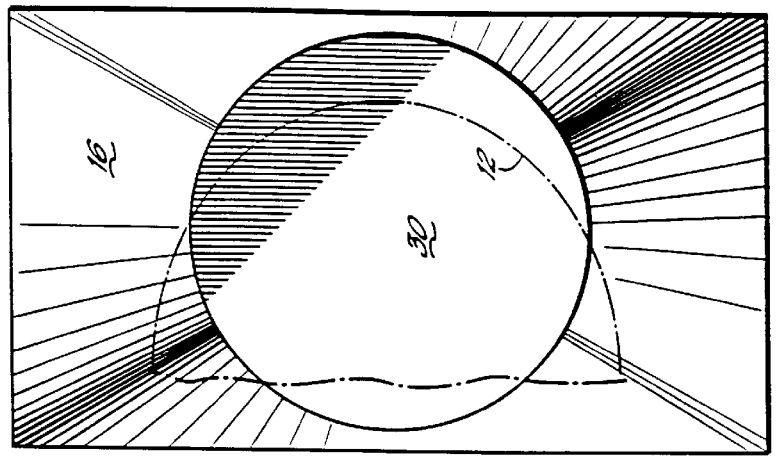
FIGS. 11A and 11B are a third embodiment of a photoacoustic breast scanner in accordance with the present invention, using an acoustic coupling tank configured to permit placement of a rotationally scanning acoustic transducer array in close proximity to a human breast.
Figure 11A:
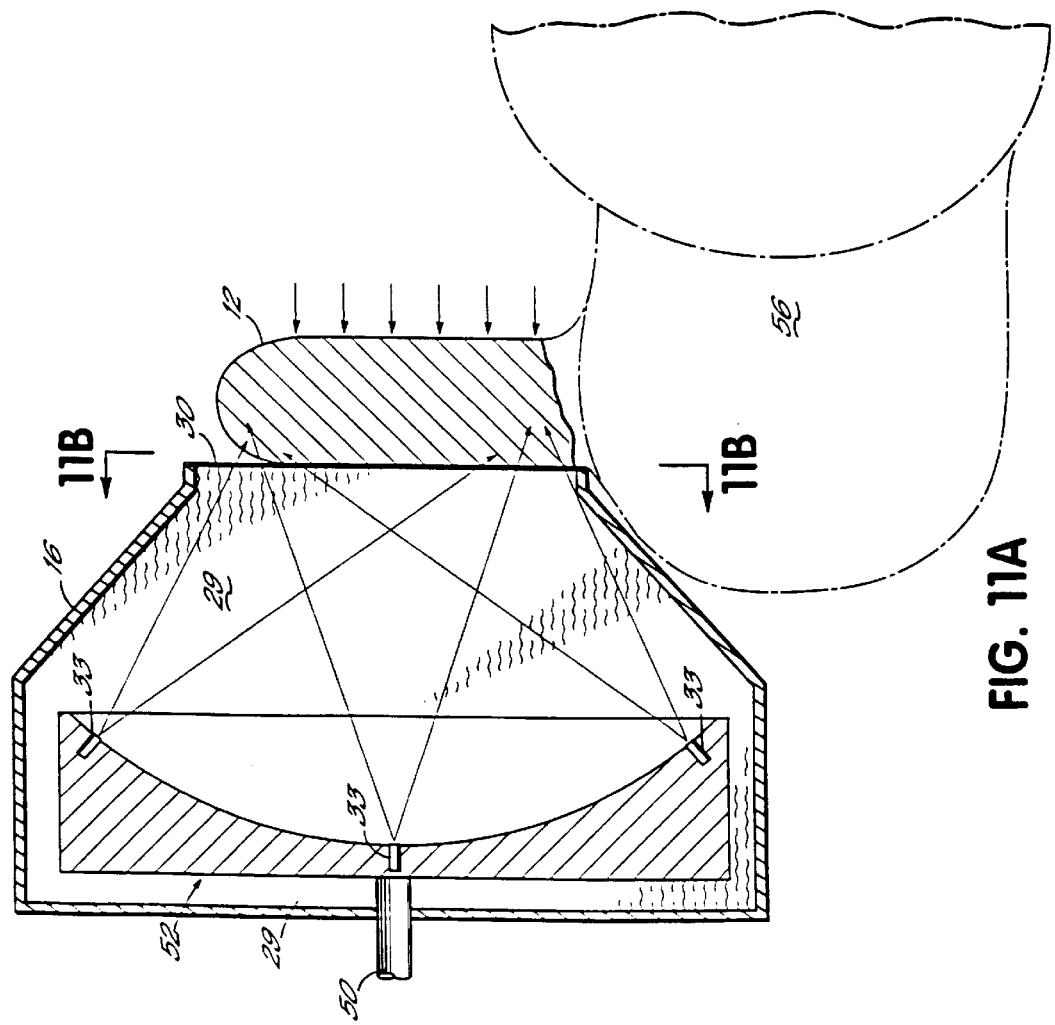

FIGS. 11A and 11B illustrate a more specific embodiment of the invention, incorporating a spherically curved spiral transducer array. Tank 16 containing acoustic media is shaped to allow the tank to be brought alongside the body 56 of a patient to be examined. The breast 12 of the patient is compressed against the flexible sheet 30 to facilitate acoustic imaging. A source of radiation, either microwave, visible or infrared, is placed in contact with the opposite side of the breast 12 to stimulate photoacoustic waves from the breast tissue. Transducers 33 are mounted on a spherically curved surface 52 such that their axes are directed toward the center of the radius of curvature of the surface 52, resulting in a large region of sensitivity overlap as previously illustrated in FIG. 9.

The spherical array 52 is rotated by a stepper motor on a support shaft 50 which is journalled within tank 16. A suitable stepper motor controller (PC board) can be obtained from New England Affiliated Technologies. The transducer array may be formulated from a monolithic, annular array of five mm diameter elements, arranged in a spiral pattern as discussed above. Satisfactory results have been achieved using low-Q ceramic transducers having a wide band frequency response from 200 kHz to 2 MHZ, falling to zero near 4 MHZ.

Figure 12:
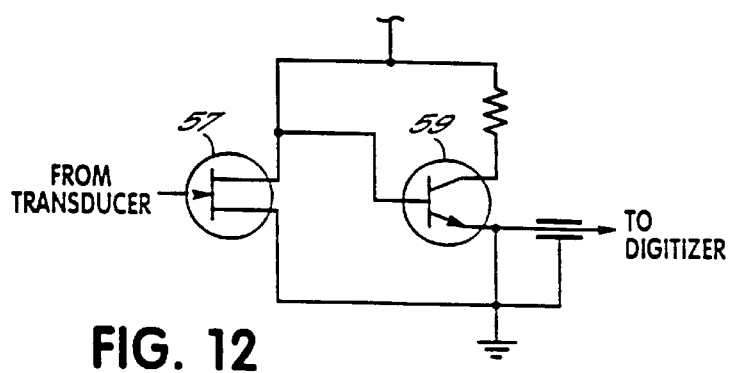
FIG. 12 is a circuit diagram of an integral transducer signal amplifier for a photoacoustic breast scanner.

The annular array is encased in an aluminum-shielded housing in which preamplifiers and line drivers are incorporated. Referring to FIG. 12, a suitable amplifier circuit can be constructed from a JFET 57 and bipolar transistor 59 arranged in a dual-stage amplifier. Signals output from the integral amplifier/line drivers are led outside of tank 16 using ultra-thin coaxial cable cables, to an external amplifier and analog-to-digital converter.

Figure 13:
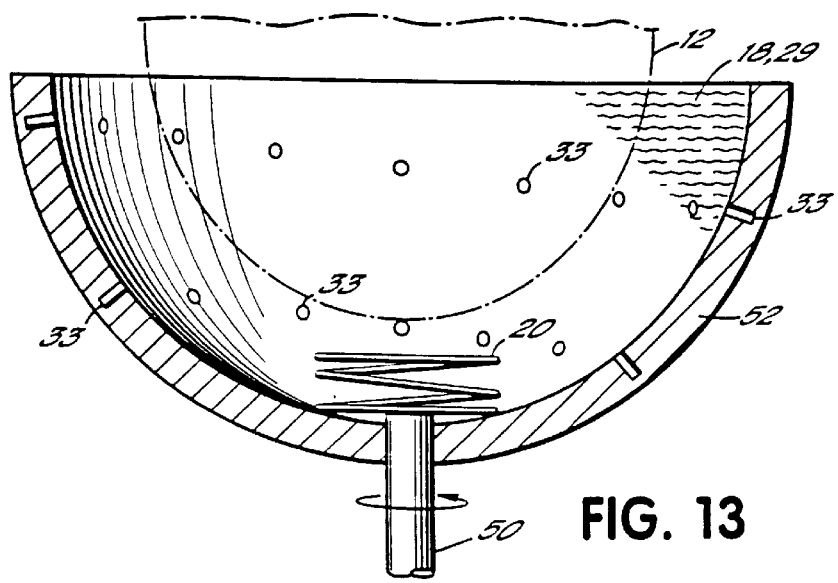
FIG. 13 is a fourth embodiment of a photoacoustic breast scanner in accordance with the present invention, using an acoustic coupling tank configured to permit a rotationally scanning acoustic transducer array to surround a human breast.

FIG. 13 illustrates another embodiment of the invention, specifically adapted for human breast imaging, in which the angle $\phi_{max}-\phi_{min}$ of spherically curved surface 52 is substantially larger than in the preceding embodiment. In this embodiment, the microwave source is a helical, "end-launch" antenna 20, for which the spherically curved, conductive surface of the spherical transducer array 52 serves as a ground plane. Surface 52 also serves as a tank for containing an acoustic and electromagnetic coupling media 18/29. (Distilled and deionized water serves as a suitable acoustic/electromagnetic coupling media.) The breast is suspended vertically into the coupling media 18/29 as illustrated, to permit coupling of both microwave energy into the breast and acoustic energy out of the breast. The individual transducers 33 are arranged as a spherical, spiral array as previously described, and the surface 52 is rotated on shaft 50 to collect an even distribution of samples from the transducers.

After sonic pressure waves are recorded using one of the embodiments of the invention described above, photoacoustic images must be "reconstructed" from multiple pressure signals. The aim is to reconstruct some property of the breast from an ensemble of pressure measurements made externally to the breast. In this case, these measurements are time-dependent pressure signals recorded subsequent to object-irradiation by a short pulse of radiation.

Figure 14:
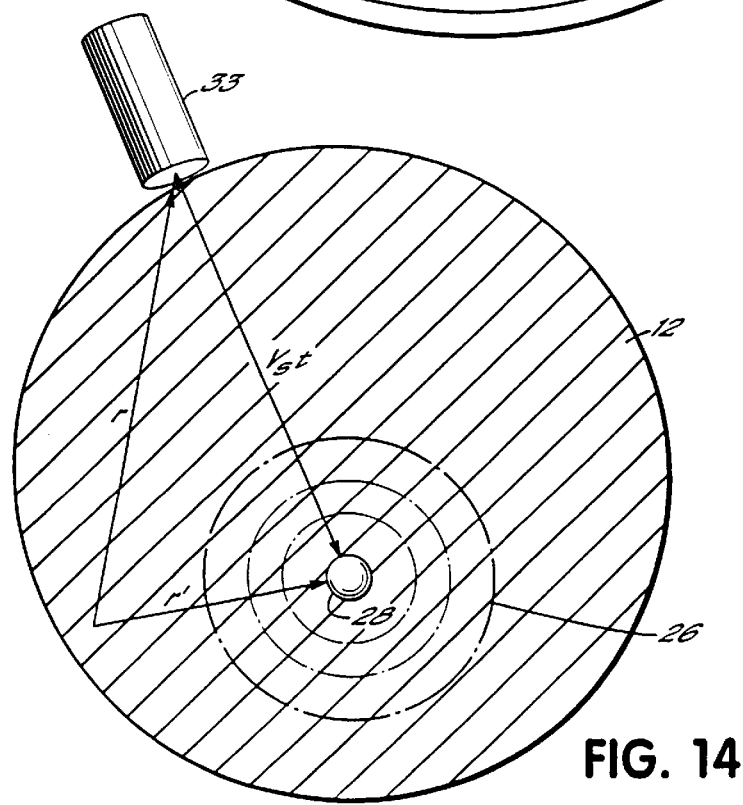
FIG. 14 illustrates the geometric relationships involved in the reconstruction methodologies used to generate a tissue image.

The generalized reconstruction geometry is illustrated in FIG. 14. The excess pressure p(r,t) that arrives at position r, where transducer 33 is located, at time t, is the sum of the pressure waves produced at all positions within the tissue. This sum can be expressed as a volume integral:

$$p(r,t) = \frac{\beta \rho}{4\pi} \int \int \int \frac{dr'}{|r-r'|} \frac{\partial^2 T(r',t')}{\partial t^2} \quad (1)$$

where $\rho$ is the mass density and $\beta$ is the coefficient of thermal expansion of the tissue, the volume integral is carried out over the entire r'-space where the temperature acceleration $\partial^2 T(r',t')/\partial t'^2$ is non-zero, and where $t'=t-|r-r'|/v_s$ ($|r-r'|/v_s$ being the time delay for an acoustic pressure wave to propagate from position r' to position r at the speed of sound in tissue $v_s$).

Under the assumption that the radiation pulse which causes the temperature acceleration is of a duration $\tau$ which is short enough ($\tau < 1\ \mu s$) to generate an adiabatic expansion of absorptive tissue, the preceding equation can be rewritten in terms of a regional heat absorption function S(r',t):

$$p(r,t) = \frac{\beta \rho}{4\pi C} \int \int \int \frac{\partial S(r',t')}{\partial t'} \frac{dr'}{|r-r'|} \quad (2)$$

where C is the specific heat of tissue. We can further write the heating-function as the product of a purely spatial and a purely temporal component, i.e., $$S(r',t') = I_0 R(r') T(t') \quad (3)$$

where $I_0$ is a scaling factor proportional to the incident radiation intensity and R(r') represents the fractional energy absorption of r'. Defined in this way $I_0 T(t')$ describes the irradiating field and R(r') describes the absorption properties of the medium (breast). The excess pressure can then be written as:

$$p(r,t) = \frac{\beta I_0}{4\pi C} \int \int \int R(r') \frac{dT(t')}{dt'} \frac{dr'}{|r-r'|} \quad (4)$$

Equation 4 expresses how the time-sequential information conveyed by the pressure signal delivers spatial information about the absorption properties of the medium.

To further simplify, both sides of equation (4) are integrated in time and multiplying factors are moved to the left, to obtain:

$$\frac{4\pi C}{\beta I_0} \int_0^t p(r,t'') dt'' = \int \int \int R(r') \frac{dr'}{|r-r'|} T(t') \quad (5)$$

Now, assuming that the temporal distribution of the irradiating field is of unit height and duration $\tau$ (see the function E(t) illustrated in FIG. 3), T(t') has a value of 1 only from t'=0 to t'=$\tau$. As a result, the integrand on the right side of equation (5) will have a value of zero everywhere except along a thin, spherical "shell" of inner radius vat surrounding point r, where $0 < t' < \tau$, i.e., where $|r-r'|/v_s < t < \tau + |r-r'|/v_s$. This thin "shell" has a thickness of $v_s \tau$; accordingly, the volume integral for this thin "shell" can be approximated by $v_s \tau$ multiplied by the surface integral, over the inner surface of the "shell", i.e., where $|r-r'|/v_s = t$, i.e.:

$$\frac{4\pi C}{\beta I_0} \int_0^t p(r,t'') dt'' \approx v_s \tau \int \int_{t=|r-r'|/v_s} R(r') \frac{dr'}{|r-r'|} \quad (6)$$

Finally, noting that $|r-r'| = v_s t$, and rearranging terms, we can define the "projection" at the position r, $S_r(t)$, as $$S_r(t) = \frac{4\pi Ct}{\beta I_0 \tau} \int_0^t p(r,t'') dt'' \approx \int \int_{t=|r-r'|/v_s} R(r') dr' \quad (7)$$

Equation (7) shows that the integral of all pressure waves received at a transducer at position r and up to time t, is proportional to the sum of the absorption function over a spherical surface a distance $v_s t$ from the transducer. Accordingly, an image of R(r') can be reconstructed by mapping integrated pressure data acquired at multiple transducers, over spherical surfaces (to create three-dimensional image) or co-planar arcs (to create a two-dimensional image).

Figure 15:
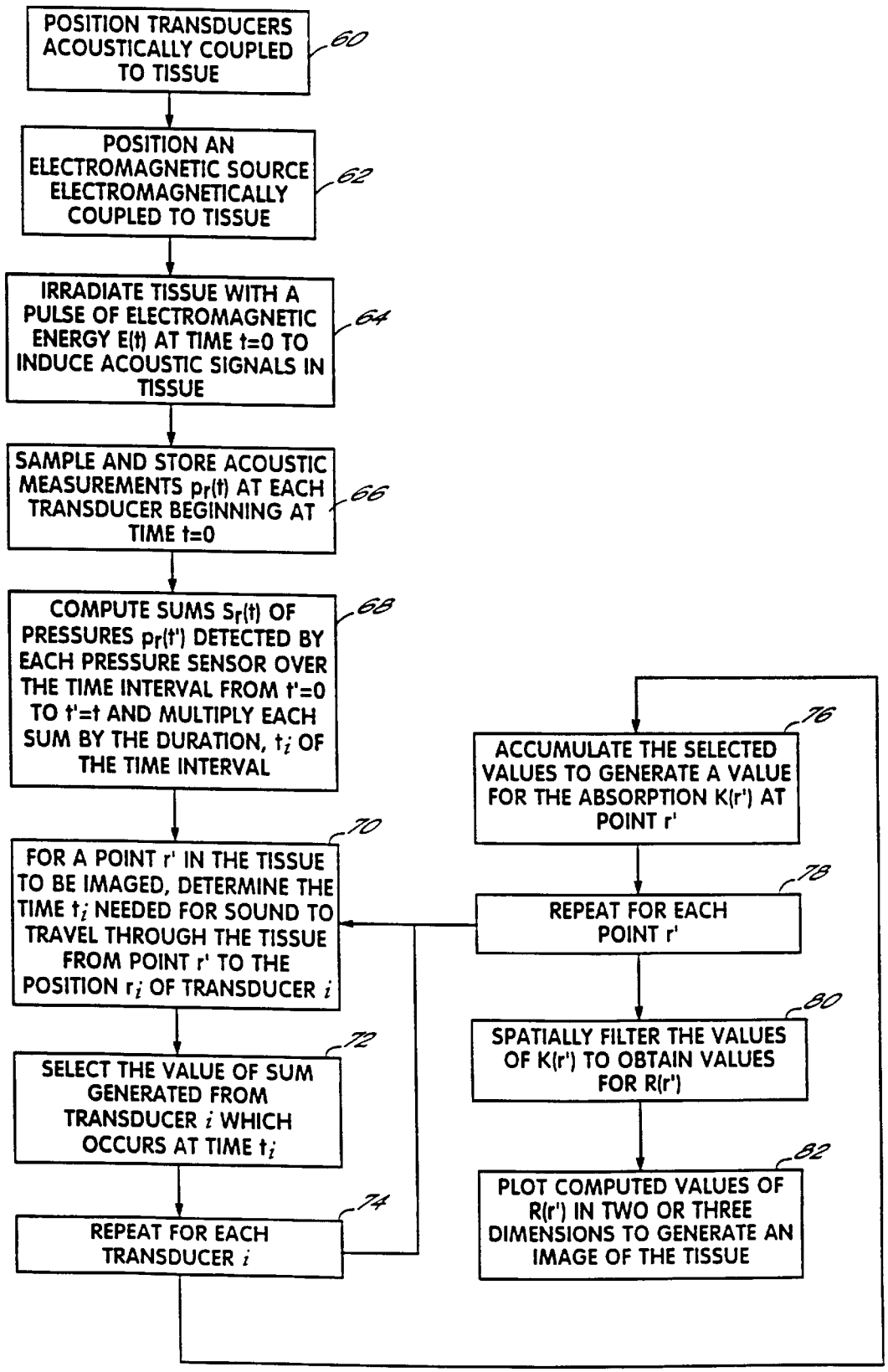
FIG. 15 illustrates a reconstruction methodology for forming a tissue image from acoustic transducer signals.

Specifically, referring to FIG. 15, this method of image reconstruction comprises:

1. Positioning transducers acoustically coupled to the tissue under study (step 60).

2. Positioning an electromagnetic source electromagnetically coupled to the tissue under study (step 62).

3. Irradiating the tissue with a brief pulse of electromagnetic energy E(t) at time t=0 to induce acoustic signals in the tissue (step 64).

4. Sampling and storing pressure measurements $P_i(t)$ at each transducer i beginning at time t=0 (step 66).

5. Computing the sums $$S_i(t) = t \sum_i p_i(t')$$

of pressure signals (step 68).

6. For a point r' in the tissue to be imaged, determining the time delay $t_i$ needed for sound to travel from point r' to the position $r_i$ of transducer i (step 70), selecting the is value of the sum $S_i(t_i)$ (generated from transducer i) which occurs at time $t_i$ (step 72), repeating these steps for each transducer i (step 74), and then accumulating the selected values $S_i(t_i)$ to generate a value K(r') at position r' according to $$K(r') = A \sum_{i=1}^{N} S_i \left( \frac{|r_i - r'|}{v_s} \right) \quad (8)$$

(step 76).

8. Repeating step 7 for each point r' to be imaged (step 78).

9. Spatially filtering the resulting values of K(r') to obtain values for R(r'). This filtering can be performed in the frequency domain using a function having a response proportional to the square of frequency. Alternatively, filtering may be performed by computing the Laplacian of the three-dimensional spatial function K(r'), i.e., R(r')=A·$\nabla^2$K(r') (9) (Step 70).

10. Plotting the values of R(r') as an image of the tissue (step 82).

Figure 16:
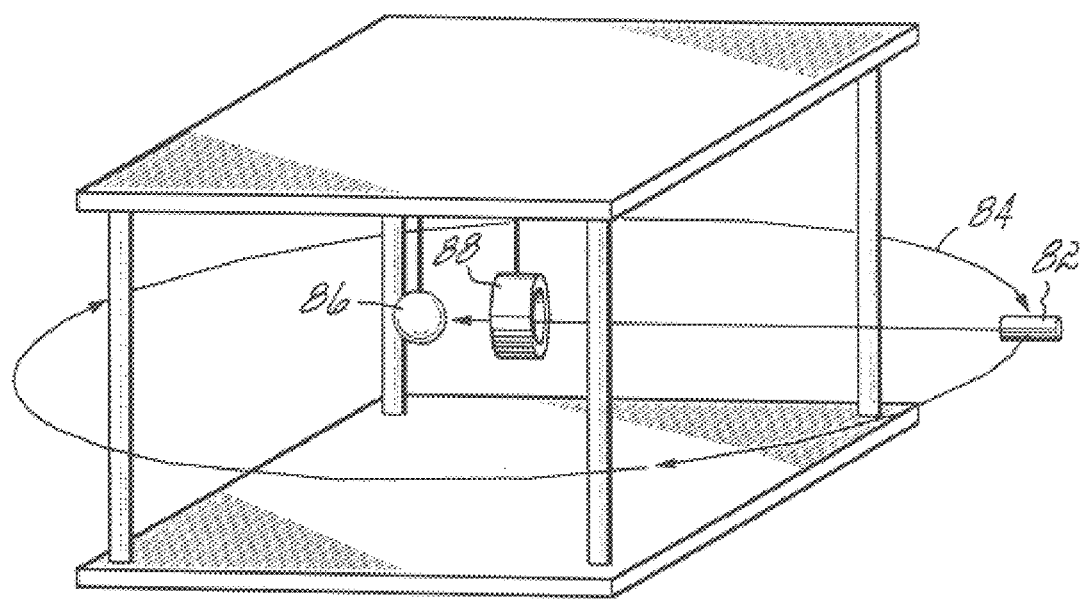
FIG. 16 is an experimental apparatus used to generate an image of an absorption phantom generally in accordance with the methodology of FIG. 15.

This reconstruction methodology was generally tested for a two-dimensional image, by constructing the simplified experimental test bed illustrated in FIG. 16. The test bed included a wideband transducer 82 with a center frequency of 2 MHZ, mounted on a 150 mm arm that was rotated along a circular path 84 under stepper-motor control. The transducer was 50 mm (height)×6 mm (width) and had a radius of curvature of 150 mm along the long dimension. The transducer was asymmetrical and focused in one dimension radially inwardly with respect to path 84; accordingly, the transducer was most responsive to acoustic signals received over a wide angle within the horizontal plane of circular path 84.

The scanning mechanism was immersed in a 50 ml/l concentration Intralipid-10%, a fatty emulsion frequently used as a tissue-mimicking scattering medium. The scattering coefficient ($\mu_s$) for Intralipid-10% @ 1.064 $\mu$m was measured as 0.015 mm$^{-1}$/ml/l. This is close to the 0.013 mm$^{-1}$/ml/l reported by van Staveren. (See van Staveren, H. J., et al., "Light scattering in Intralipid-10% in the wavelength range of 400–1100 nm", *Applied Optics*, 31(1) :4507–4514 (1991).) Using a value of 0.48 for the mean cosine of scatter (g), as reported by van Staveren, and the scattering coefficient measured in our laboratory, the 50 ml/l concentration of Intralipid-10% produced a reduced scattered coefficient $\mu_s'$=0.39 mm$^{-1}$ [$\mu_s' \equiv (1-g)\mu_s$]. At this wavelength, the absorption of Intralipid-10% is due almost entirely to the absorption of water, $\mu_a \equiv 0.0164$ mm$^{-1}$. These values are a factor of 2–3 less than those measured in vitro for different types of breast tissue at 900 nm.

A 50 mm diameter laser beam from a pulsed Nd:YAG laser ($\lambda$=1.064 $\mu$m, pulse width<10 ns, 20 Hz repetition rate, 250 mJ/pulse) illuminated the scattering medium from below. The imaging plane of path 84 was normal to the laser beam and was located 47.5 mm above the bottom surface of the scattering medium. The laser beam axis and rotational axis of the transducer scanning arm were coincident.

Data acquisition proceeded as follows: The transducer was stepped through 360° at 2° increments along path 84. At each angle, the temporal acoustic signal recorded by the transducer was digitized to 12 bits at a rate of 10 MHZ for a total of 1024 samples. The sampling interval was synchronized to the pulsing of the laser. At each angle, the temporal acoustic signal for 16 consecutive pulses were averaged. This procedure was repeated for 180 angles.

The absorption phantom illustrated in FIG. 16 was used in imaging. It consisted of a 4 mm diameter, black, latex ball 86 and a black, rubber cylinder 88 suspended on two, 0.35 mm diameter, clear, polyethylene threads. The dimensions for the cylinder were 8.5 mm outside diameter 5.0 mm inside diameter and 4 mm length.

Figure 17:
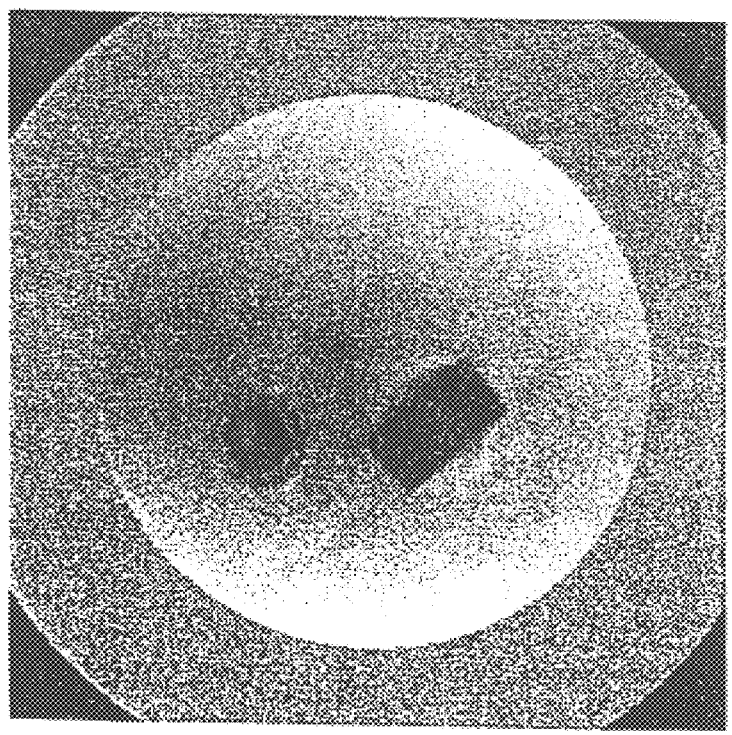
FIG. 17 is the image created therefrom.

Image reconstruction proceeded using an adaptation of the integrated, filtered-back projection algorithm described above, applicable to a two-dimensional image. The $S_r(t)$ were computed for each of the 180 transducer angles, backprojected over appropriate arcs and summed. A value of $v_s$=1.5 mm/$\mu$s was assumed. The next step was to apply a 2-D filter. Filtering was performed in the frequency domain using a linear ramp function a cosine-weighted apodizing window, i.e., F($f$)=|$f/f_n$|*(1+cos($\pi f/f_n$))/2, where $f$ is the spatial frequency and $f_n$ is the Nyquist frequency associated with the reconstruction matrix. In this instance, $f_n$=3 cycles/mm. The center 30 mm region of the reconstruction is displayed in FIG. 17.

The basic relationship between an acoustic signal and a heterogeneous distribution of absorbed energy is given by Equation 7. At any moment in time following an irradiating optical pulse, the temporally weighted and temporally integrated acoustic pressure up to that time is proportional to a surface integral of the absorbed heat distribution R(r) within the object being imaged. This relationship is true, provided the irradiating optical pulse is short enough and sharp enough. This condition is met for optical pulses of less than 1 $\mu$s duration.

In order to "reconstruct" R(r') from a set of acoustic measurements, data must be sampled over at least 2$\pi$ steradians. In the restricted case, where significant optical absorption takes place within a narrow plane, R(r') can be reconstructed using a set of co-planar acoustic data acquired over 360°. The image displayed in FIG. 17 was reconstructed under these conditions. This image reflects what one would expect: a "cut" through the center of a spherical and cylindrical absorber. It is of note that a "halo" artifact surrounds the image of the latex ball 86. This originates from the decreased velocity of sound within the latex ball (1.0 mm/$\mu$s) compared to the Liposyn-10% solution (1.5 mm/$\mu$s).

Were R(r') distributed throughout a larger volume, it would have been necessary to obtain acoustic data over the surface of a hemisphere in order to adequately reconstruct R(r'). Such an operation can be performed by the transducer geometries described above.

Further details on the above experimental arrangement can be found in Kruger et al., "Photoacoustic ultrasound (PAUS)—Reconstruction tomography", *Medical Physics* 22(10):1605–1609 (October 1995), incorporated by reference herein in its entirety.

A second methodology for image generation can also be derived from Equations (8) and (9). Specifically, it can be shown that the Laplacian of the back-projection of the time-weighted, integrated pressure signals is approximately equal to the back-projection of the first time derivative of the pressure signal, if the radius R of any imaged object is small, i.e., where |r–r'|>>R, as follows:

$$R(r') = A \sum_{i=1}^{N \times M} t_i \frac{d\, p_i(t_i)}{d\, t} \quad (10)$$

where $t_i = |r_i - r'|/v_s$, r' is a vector that denotes the location within the tissue, $r_i$ is a vector that denotes the location of transducer i, $v_s$ is the velocity of sound, A is a constant, and $p_i(t_i)$ is the samples of the pressure signal that reaches the i-th transducer.

Referring to FIG. 18, using this approximation, the steps in the reconstruction process are as follows:

1. Positioning transducers acoustically coupled to the tissue under study (step 114).

2. Positioning an electromagnetic source electromagnetically coupled to the tissue under study (step 116).

3. Irradiating the tissue with brief pulse of electromagnetic energy E(t) at time t=0 to induce acoustic signals in tissue (step 118).

4. Sampling and storing pressure measurements $p_i(t)$ at each transducer beginning at time t=0 (step 120).

5. Calculating the time-weighted, first temporal derivative of $p_i(t_i)$, i.e., $t_i(dp_i(t_i)/dt)$, for each of the i transducers (step 122).

6. For each position, r', in the tissue, summing the selected values of the time-weighted first temporal derivatives of the pressure signals from each transducer as indicated in Equation 9 (steps 124–132).

7. Generating an image of the tissue from computed values of R(r') (step 134).

This reconstruction procedure produces three-dimensional images of the energy deposition within the interior of the tissue, which is representative of the differential absorption of the irradiating energy by the different types of tissues within the tissue.

To perform the above calculation, it is necessary to obtain the first time-derivative of the pressure signal that reaches each transducer. It should be noted, however, that a transducer produces a characteristic "ringing" in its electrical response to an externally-applied pulse of pressure, which distorts the shape of the electrical output of the transducer away from that of the pressure waveform. Referring to FIG. 19, this ringing response 136 approximates the impulse response of the transducer 33, i.e., the electrical signal as a function of time that is produced when a very abrupt pressure impulse 138 strikes the transducer.

If a transducer were fabricated to produce a simple biphasic (or "doublet") response to an impulse of pressure, that is one positive lobe, followed a short time later by one negative lobe (an ideal response 136 is illustrated in FIG. 19), then the electrical output of the transducer would be approximately proportional to the first time-derivative of the input pressure signal. This would be desirable, because it would eliminate the necessity of computing the first time-derivative of the input pressure signal; rather, the time derivative would be produced by the transducer in the first instance.

For any real transducer, however, such a response would be difficult to achieve. Rather, the impulse response of a transducer is closer to a damped sinusoid, as is illustrated in waveform 140 (p(t)) in FIG. 20. In this example, the impulse response of the transducer is assumed to be of the form $p(t)=\sin(2\pi ft)e^{aft}$. Such a response displays a periodic component of a characteristic temporal frequency $f$, that decays exponentially with time.

Figure 20:
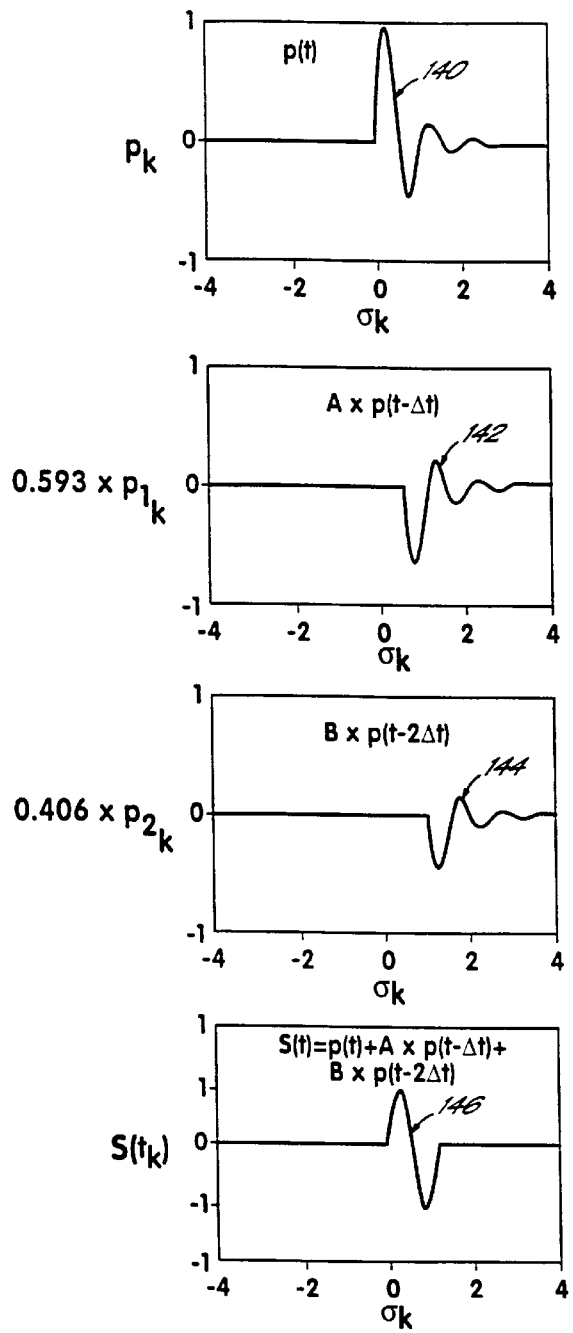
FIG. 20 illustrates a simulated actual impulse response and a methodology for converting this impulse response to an approximation of the ideal response illustrated in FIG. 19.

In this case, an approximate "differential" transducer response can by synthesized by delaying the originally recorded pressure waveform, p(t), by varying amounts, weighing the delayed pressure signals, and summing the delayed pressure signals together with the original waveform. An example is illustrated in FIG. 20, which shows two weighted, time-delayed waveforms (Ap(t−Δt) 142 and Bp(t−2Δt) 144 (where Δt is ½f) generated from the assumed impulse response 140 of the transducer. When the time-delayed waveforms 142 and 144 are added to the response 140 of the transducer, the resulting waveform 146 synthesizes a biphasic impulse response S(t).

Thus, to implement the reconstruction algorithm described above, the transducer responses can be synthesized to be differential in nature using the methodology illustrated in FIG. 20, after which the output of each transducer will be proportional to dp(t)/dt.

Figure 21:
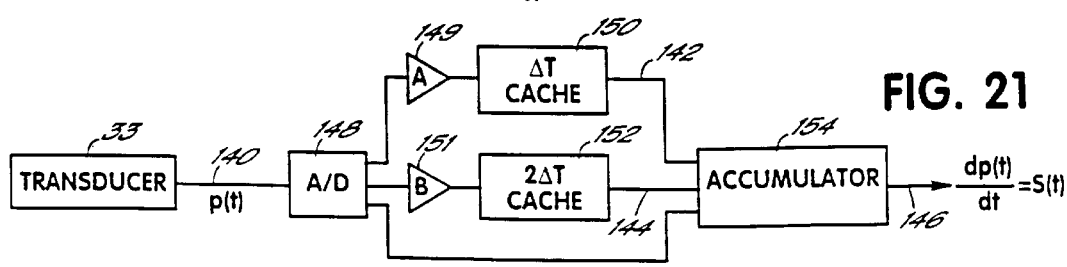
FIG. 21 is a circuit diagram of a circuit for performing the conversion methodology of FIG. 20.

Referring to FIG. 21, a circuit for performing such a reconstruction includes an analog-to-digital converter 148 for converting the analog signal from the transducer to an equivalent digital signal, an amplifier 149 and cache 150 for receiving and temporarily storing samples from A/D converter 148 and outputting the sample which was stored Δt earlier multiplied by a gain factor A, a second amplifier 151 and cache 152 for storing samples and outputting the sample which was stored 2Δt earlier multiplied by a gain factor B, and a digital accumulator 154 for summing the outputs of caches 148 and 150 with the current sample from the A/D converter to produce an output digital signal S which is representative of dp(t)/dt.

Using a circuit such as that shown in FIG. 21, steps 120 and 122 of the reconstruction process described by FIG. 18 can be accomplished in a single operation by hardware rather than in software computations, increasing the scanning and imaging rate of the apparatus.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. Apparatus for imaging tissue structures by detecting acoustic waves originating in the tissue, comprising a tank containing a coupling media having an acoustic characteristic impedance which is substantially similar to that of the tissue to reduce reflections of acoustic waves impinging into the coupling media from the tissue;

a three-dimensional curved surface immersed in the tank and positioned opposite to the tissue; and a plurality of acoustic sensors positioned upon the three dimensional curved surface and directed toward the tissue to detect acoustic waves originating in the tissue for use in imaging said tissue structure.

2. The apparatus of claim 1 further comprising a motor connected to the curved surface and moving the surface to collect acoustic waves from the sensors in a plurality of locations.

3. The apparatus of claim 2 wherein the motor is a rotating motor and rotates the curved surface and sensor to a plurality of rotational positions.

4. The apparatus of claim 1 wherein the curved surface is spherically curved.

5. The apparatus of claim 1 wherein the sensors are positioned on the curved surface along a spiral path.

6. The apparatus of claim 1 further comprising an electromagnetic radiation source positioned inside of the tank and immersed in the coupling media, and wherein the curved surface is conductive and forms a ground plane for the electromagnetic radiation source.

7. A method for imaging tissue structures by detecting acoustic waves originating in the tissue, comprising immersing the tissue in a coupling media having an acoustic characteristic impedance which is substantially similar to that of the tissue to reduce reflections of acoustic waves impinging into the coupling media from the tissue;

immersing a three-dimensional curved surface immersed in the coupling media positioned opposite to the tissue; and detecting acoustic waves originating in the tissue with a plurality of acoustic sensors positioned upon the three dimensional curved surface for use in imaging said tissue structure.

8. The method of claim 7 further comprising moving the curved surface to a plurality of locations and collecting acoustic waves with the sensors in each of the plurality of locations.

9. The method of claim 8 wherein moving the curved surface to a plurality of locations comprises rotating the curved surface to a plurality of rotary positions.

10. The method of claim 7 wherein the curved surface is spherically curved.

11. The method of claim 7 wherein the sensors are positioned on the curved surface along a spiral path.

12. The method of claim 7 further comprising irradiating the tissue with an electromagnetic radiation source positioned inside of the tank and immersed in the coupling media, wherein the curved surface is conductive and forms a ground plane for the electromagnetic radiation source.

13. Apparatus for imaging tissue structures by detecting acoustic waves originating in, returning from or passing through the tissue, comprising
- a tank containing a coupling media having an acoustic characteristic impedance which is substantially similar to that of the tissue to reduce reflections of acoustic waves impinging into the coupling media from the tissue;
- a three-dimensional bowl-shaped smoothly curved surface immersed in the tank and positioned opposite to the tissue; and
- a plurality of acoustic sensors positioned upon the three dimensional curved surface and directed toward the tissue to detect acoustic waves originating in, returning from or passing through the tissue for use in imaging said tissue structure.

14. The apparatus of claim 13 further comprising a motor connected to the curved surface and moving the surface to collect acoustic waves from the sensors in a plurality of locations.

15. The apparatus of claim 14 wherein the motor is a rotating motor and rotates the curved surface and sensor to a plurality of rotational positions.

16. The apparatus of claim 13 wherein the curved surface is spherically curved.

17. The apparatus of claim 13 wherein the sensors are positioned on the curved surface along a spiral path.

18. The apparatus of claim 13 further comprising an electromagnetic radiation source positioned inside of the tank and immersed in the coupling media, and wherein the curved surface is conductive and forms a ground plane for the electromagnetic radiation source.

19. A method for imaging tissue structures by detecting acoustic waves originating in, returning from or passing through the tissue, comprising
- immersing the tissue in a coupling media having an acoustic characteristic impedance which is substantially similar to that of the tissue to reduce reflections of acoustic waves impinging into the coupling media from the tissue;
- immersing a three-dimensional bowl-shaped smoothly curved surface immersed in the coupling media positioned opposite to the tissue; and
- detecting acoustic waves originating in, returning from or passing through the tissue with a plurality of acoustic sensors positioned upon the three dimensional curved surface for use in imaging said tissue structure.

20. The method of claim 19 further comprising moving the curved surface to a plurality of locations and collecting acoustic waves with the sensors in each of the plurality of locations.

21. The method of claim 20 wherein moving the curved surface to a plurality of locations comprises rotating the curved surface to a plurality of rotary positions.

22. The method of claim 19 wherein the curved surface is spherically curved.

23. The method of claim 19 wherein the sensors are positioned on the curved surface along a spiral path.

24. The method of claim 19 further comprising irradiating the tissue with an electromagnetic radiation source positioned inside of the tank and immersed in the coupling media, wherein the curved surface is conductive and forms a ground plane for the electromagnetic radiation source.

* * * * *